United States Patent
Framer

(10) Patent No.: US 7,594,287 B2
(45) Date of Patent: Sep. 29, 2009

(54) HOSPITAL SHEET OR BLANKET

(76) Inventor: Evelyn Framer, 5500 Collins Ave., Apt. 702, Miami, FL (US) 33140

( * ) Notice: Subject to any disclaimer, the term of this patent is extended or adjusted under 35 U.S.C. 154(b) by 0 days.

(21) Appl. No.: 11/299,716

(22) Filed: Dec. 12, 2005

(65) Prior Publication Data

US 2007/0130691 A1    Jun. 14, 2007

(51) Int. Cl.
A47G 9/04    (2006.01)
A61B 19/08    (2006.01)
(52) U.S. Cl. ............... 5/495; 5/496; 128/849; 128/853
(58) Field of Classification Search ............ 5/494–496, 5/500, 502, 922, 923; 128/872, 849–854
See application file for complete search history.

(56) References Cited

U.S. PATENT DOCUMENTS

| | | | | |
|---|---|---|---|---|
| 1,735,521 A | * | 11/1929 | Young | 5/494 |
| 1,825,520 A | * | 9/1931 | Grunfeld | 2/69 |
| 1,859,820 A | * | 5/1932 | Eaker | 2/69.5 |
| 1,863,256 A | * | 6/1932 | Snoddy | 5/494 |
| 1,875,525 A | * | 9/1932 | Thexton et al. | 5/494 |
| 1,885,558 A | * | 11/1932 | Smith | 128/872 |
| 1,929,263 A | * | 10/1933 | Sork | 2/69.5 |
| 2,037,216 A | * | 4/1936 | Eshlin | 5/494 |
| 2,062,611 A | * | 12/1936 | Rosenthal | 5/494 |
| 2,151,434 A | * | 3/1939 | Malah | 128/872 |
| 2,248,768 A | * | 7/1941 | Licht | 5/485 |
| 2,345,592 A | * | 4/1944 | Friedman | 128/872 |
| 2,576,207 A | * | 11/1951 | Belden | 5/494 |
| 2,720,661 A | * | 10/1955 | Harris | 5/494 |
| 2,722,694 A | * | 11/1955 | Bryant | 128/872 |
| 3,121,885 A | * | 2/1964 | Cherry | 128/872 |
| 3,241,161 A | * | 3/1966 | Dashosh | 5/501 |
| 3,962,738 A | * | 6/1976 | Menditto | 5/494 |
| 4,317,245 A | * | 3/1982 | El-Amin | 5/497 |
| 4,507,805 A | * | 4/1985 | Calutoiu | 2/69.5 |
| 4,839,934 A | * | 6/1989 | Rojas | 5/502 |
| 4,860,771 A | | 8/1989 | Burgos et al. | |
| 4,993,090 A | * | 2/1991 | Ranalli | 5/482 |
| 5,070,561 A | | 12/1991 | Keidser et al. | |
| 5,072,875 A | | 12/1991 | Zacoi et al. | |
| 5,187,825 A | * | 2/1993 | Tesch | 5/502 |
| 5,304,213 A | | 4/1994 | Berke et al. | |
| 5,515,868 A | | 5/1996 | Mills | |

(Continued)

Primary Examiner—Robert G Santos
(74) Attorney, Agent, or Firm—Pabst Patent Group LLP

(57) ABSTRACT

Coverings, such as sheets or blankets, for use in medical settings are described herein. The coverings contain one or more closable slits or openings. In the preferred embodiment, the covering contains two slits. One slit is along the length of the material, in the center of the covering, and a second slit is perpendicular to the first slit. Thus, when used to cover a patient, the first slit generally runs along the length of a patient's body, and the second slit generally runs across the width of the patient's upper torso and outstretched arms. The slits or openings, or portions thereof, can be closed as desired by any suitable fastener, such as snaps, zippers, tape, buttons, or hook and loop fasteners. The closable slits allow a patient to remain covered while receiving the necessary medical care. Optionally, the covering contains one or more pockets. The covering may be made of any washable natural or synthetic material or blend thereof. Optionally the covering is disposable, and preferably it is formed from a degradable material.

17 Claims, 1 Drawing Sheet

U.S. PATENT DOCUMENTS

| | | |
|---|---|---|
| 5,773,275 A | 6/1998 | Anderson et al. |
| 5,974,605 A | 11/1999 | Dickerhoff et al. |
| 5,984,910 A * | 11/1999 | Berke .......................... 604/352 |
| 6,243,896 B1 * | 6/2001 | Osuna et al. ................... 5/502 |
| 6,345,621 B1 * | 2/2002 | Chandler et al. ............. 128/849 |
| 6,640,362 B1 * | 11/2003 | Kimball ......................... 5/482 |
| 7,249,389 B2 * | 7/2007 | Russell ......................... 5/502 |
| 2007/0130691 A1 * | 6/2007 | Framer .......................... 5/495 |

* cited by examiner

HOSPITAL SHEET OR BLANKET

FIELD OF THE INVENTION

The present invention is in the field of sheets or blankets, which are particularly suitable for hospital use.

BACKGROUND OF THE INVENTION

When a patient is receiving medical care, such as in the hospital, in an emergency vehicle, or at home, tubes are often inserted into his body and one or more parts of his body must be accessed or suspended during treatment. If only one sheet or blanket is used to cover the patient, portions of his body may be exposed, resulting in exposure to temperature changes and drafts. Alternatively, multiple sheets may be used to properly cover the patient. However, this increases the cost. An improved, cost-effective covering is needed.

Therefore it is an object of the invention to provide a cost-effective covering for use in medical settings.

BRIEF SUMMARY OF THE INVENTION

Coverings, such as sheets or blankets, for use in medical settings are described herein. The sheets and blankets contain one or more closable slits or openings (generally referred to herein as "slits") along the length of the material and one or more slits or openings in the perpendicular direction to allow the placement of tubes and the exposure of only a selected portion of the body at a time. The coverings disclosed herein are also known by the trade names MORSHEET™ and MORBLANKET™. In the preferred embodiment, the covering contains two slits. One slit is along the length of the material, in the center of the covering, and a second slit is perpendicular to the first slit. Thus, when used to cover a patient, the first slit generally runs along the length of a patient's body, and the second slit generally runs across the width of the patient's upper torso and outstretched arms. The slits or openings, or portions thereof, can be closed as desired by any suitable fastener, such as snaps, zippers, tape, buttons, or hook and loop fasteners. The closable slits allow a patient to remain covered while receiving the necessary medical care. Optionally, the sheet or blanket contains one or more pockets. The sheet or blanket may be made of any washable natural or synthetic material or blend thereof. Optionally the sheet or blanket is disposable. Preferably the disposable covering is made of a degradable material.

DETAILED DESCRIPTION OF THE INVENTION

I. Coverings

Figure 1:
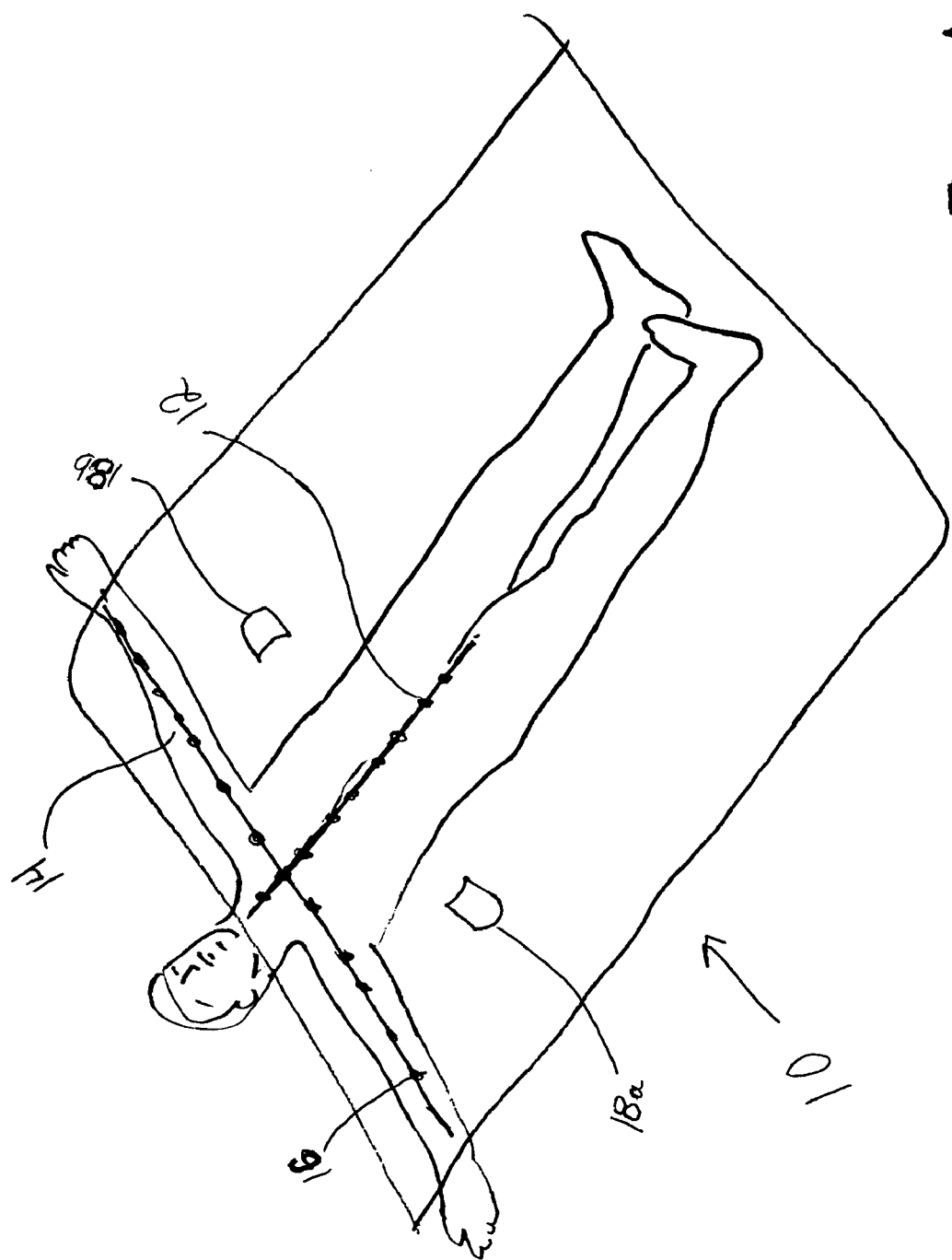
FIG. 1 is an illustration of the preferred covering.

The covering, typically a sheet or blanket, contains one or more slits along the length or width of the material forming the covering. The coverings disclosed herein are also known by the trade names MORSHEET™ and MORBLANKET™. In the preferred embodiment, the material contains two slits, where one is perpendicular to the other. In the preferred embodiment, illustrated in FIG. 1, the covering is a sheet or blanket (10), which contains one slit (12) that is located on or about the centerline along the length of the material (herein referred to as "the centerline") and a second slit (14) that is perpendicular to the first slit and is located in the upper half of the covering. When the covering is used to cover a patient, the first slit generally runs along the length of the patient's body, and the second slit generally runs across the width of the patient's upper torso and outstretched arms. Optionally, the sheet or blanket contains slits in other locations, such as along the length of the fabric approximately within 6 to 12 inches on either or both sides of the centerline (not shown in figure).

A. Fasteners

The slits or openings, or portions thereof, can be closed as desired by any suitable fastener (16), such as snaps, zippers, buttons, tape, or hook and loop fasteners. Suitable hook and loop fasteners include a material having a surface of hooks mated with material having a surface of loops (e.g. VELCRO® fasteners). Generally fasteners will be placed along the length of each slit to allow for complete or partial closure of the slit, as necessary.

B. Materials

The coverings are generally formed of a washable or degradable material. Suitable materials include natural and synthetic materials and blends thereof. Suitable natural materials include cotton and wool. Suitable synthetic materials include nylon, polyester, and acrylic and blends thereof. In one embodiment, the material is a synthetic material that heats up in the presence of moisture, such as the material sold under the trade name BREATH THERMO® (a 93% polyester/7% polyacrylate material sold by Mizuno Corp.), a fabric that generates heat from the absorption of moisture. The material may a blend of one or more natural materials with one or more synthetic materials (e.g. 50% cotton and 50% polyester). Optionally, the material is a degradable material, such as paper. The thickness of the material is determined by its use. The material may be thin, to serve as a sheet, or thick, to serve as a blanket.

C. Pockets

Optionally, the covering contains one or more pockets, in which medical instruments, containers or devices may be placed. The pocket(s) may be located anywhere on the covering, as long as they are not placed in the location of a slit. For example, as illustrated in FIG. 1, the pocket(s) (18a and 18b) may be located on the right and/or left side(s) of the centerline. The pocket(s) may be located above (also referred to herein as the "upper half") and/or below (also referred to herein as the "lower half") a line passing through the center of the blanket and perpendicular to the centerline.

II. Methods of Using the Coverings

The covering may be placed over a patient who is receiving medical care, or a patient who is recovering from an illness or medical procedure. The coverings are particularly suitable for use in medical settings, such as hospitals, in-home care or emergency vehicles, e.g. ambulances. The slits may be opened to access a portion of the patient's body, such as for the placement of an intravenous feeding tube or to draw blood. Alternatively one or more slits may be opened and a portion of the body in need of treatment or which has received treatment may be inserted through the slit and placed above the covering. For example, if a patient's fractured femur is placed in traction, the slit can be opened to allow the leg to extend out of the sheet or blanket, while the rest of the body remains covered. Optionally, a patient's head can be placed through one of the slits. In this embodiment, the sheet or blanket could be used to cover both the front and back, or a portion of the front and/or a portion of the back, of the patient. Preferably, when the patient's head is placed through one of the slits, the covering completely covers on side of the patient's body and covers only the top portion of the opposite side of the patient's body.

Those skilled in the art will recognize, or be able to ascertain using no more than routine experimentation, many equivalents to the specific embodiments of the invention described herein. Such equivalents are intended to be encompassed by the following claims.

I claim:

1. A covering comprising at least two closable slits,
   wherein the covering has a top surface, a bottom surface and a perimeter,
   wherein the slits extend through the top surface and through the bottom surface and are spaced from the perimeter,
   wherein each of the slits comprises a length and fasteners placed substantially along the length of each slit such that the fasteners selectively attach to each other when the covering is used to cover a patient,
   wherein the first slit between the respective ends of the first and second slits is located along the length of the covering and wherein the second slit runs along the width of the covering,
   wherein the second slit is perpendicular to and intersects with the first slit, and
   wherein the fasteners are selected from the group consisting of buttons, snaps, tape, and hook and loop fasteners.

2. The covering of claim 1 in the form of a sheet or a blanket.

3. The covering of claim 2, wherein the sheet or blanket is formed of a washable or degradable material.

4. The covering of claim 3, wherein the material is a natural or synthetic fabric or blend thereof.

5. The covering of claim 3, wherein the sheet or blanket is formed of a degradable material.

6. The covering of claim 2 in the form of a sheet.

7. The covering of claim 6, wherein the sheet is formed from paper.

8. The covering of claim 1, wherein the first slit is located along the length of the covering and in the center of the covering.

9. The covering of claim 1, wherein the second slit is located along the width of the covering and in the top half of the covering.

10. The covering of claim 1, wherein some of the one or more fasteners are open and some of the one or more fasteners are closed.

11. A method for covering a patient comprising placing a covering on the patient,
    wherein the covering comprises at least two closable slits,
    wherein the covering has a top surface, a bottom surface and a perimeter,
    wherein the slits extend through the top surface and through the bottom surface and are spaced from the perimeter,
    wherein each of the slits comprises a length and fasteners placed substantially along the length of each slit such that the fasteners selectively attach to each other,
    wherein the first slit is located on the centerline of the covering so that it generally corresponds with the length of the patient,
    wherein the second slit is perpendicular to and intersects with the first slit between the respective ends of the first and second slits and wherein the second slit is located in the upper half of the covering so that it generally corresponds with the width of the patient's upper torso, and
    wherein the fasteners are selected from the group consisting of buttons, snaps, tape, and hook and loop fasteners.

12. The method of claim 11, wherein the covering is formed of a washable or degradable material.

13. The method of claim 12, wherein the covering is formed of a degradable material.

14. The method of claim 11, wherein the covering is in the form of a sheet or a blanket.

15. The method of claim 14, wherein the covering is in the form of a sheet.

16. The method of claim 15, wherein the sheet is formed from paper.

17. The method of claim 11, wherein the covering covers one side of the patient and covers only the top portion of the opposition side of the patient's body.

* * * * *